United States Patent
Berlinger et al.

(10) Patent No.: US 10,926,106 B2
(45) Date of Patent: Feb. 23, 2021

(54) PATIENT PRE-POSITIONING IN FRAMELESS CRANIAL RADIOSURGERY USING THERMAL IMAGING

(71) Applicant: Brainlab AG, Munich (DE)

(72) Inventors: Kajetan Berlinger, Munich (DE); Hagen Kaiser, Icking (DE)

(73) Assignee: BRAINLAB AG, Munich (DE)

( * ) Notice: Subject to any disclaimer, the term of this patent is extended or adjusted under 35 U.S.C. 154(b) by 151 days.

(21) Appl. No.: 16/090,607

(22) PCT Filed: May 4, 2016

(86) PCT No.: PCT/EP2016/060048
§ 371 (c)(1),
(2) Date: Oct. 2, 2018

(87) PCT Pub. No.: WO2017/190780
PCT Pub. Date: Nov. 9, 2017

(65) Prior Publication Data
US 2019/0111279 A1    Apr. 18, 2019

(51) Int. Cl.
*A61N 5/10* (2006.01)
*A61B 6/00* (2006.01)
(Continued)

(52) U.S. Cl.
CPC ............ *A61N 5/103* (2013.01); *A61B 6/00* (2013.01); *A61B 6/032* (2013.01); *A61B 6/0487* (2020.08);
(Continued)

(58) Field of Classification Search
CPC .... A61N 5/10; A61B 6/04; A61B 6/03; G06T 7/37; G06T 7/33; G06T 7/70; G06T 7/13
See application file for complete search history.

(56) References Cited

U.S. PATENT DOCUMENTS 5,668,847 A * 9/1997 Hernandez ............... A61N 5/10
378/65
7,348,974 B2 * 3/2008 Smith .................. A61N 5/1049
345/420
(Continued)

FOREIGN PATENT DOCUMENTS

EP        1 563 799 A1    8/2005
WO    2004000097 A2   12/2003
(Continued)

OTHER PUBLICATIONS

Office Action for corresponding European application No. 16721414.7-1210 dated Jul. 1, 2019.
(Continued)

Primary Examiner — Mia M Thomas
(74) Attorney, Agent, or Firm — Tucker Ellis LLP

(57) ABSTRACT

A method and system supports pre-positioning a patient for treatment by radiotherapy or radiosurgery. The disclosed method encompasses comparing an image of a reference structure having a known position relative to an anatomical body part of a patient, such as a live thermal/infrared image of the reference structure, to a predetermined medical image of the reference structure associated with a known position relative to a reference position, such as a known isocenter of a radiotherapy or radiosurgery apparatus. On that basis, it is determined whether the reference structure has moved relative to the reference position. A decision may be made to determine whether the reference structure and therefore the patient has been correctly positioned and/or kept in his desired position relative to a treatment device, and to compensate for any possible positional deviation by moving the patient.

17 Claims, 7 Drawing Sheets

(51) Int. Cl.
*G06T 7/73* (2017.01)
*A61B 6/04* (2006.01)
*G06T 7/13* (2017.01)
*G06T 7/33* (2017.01)
*G06T 7/37* (2017.01)
*G06T 7/70* (2017.01)
*A61B 6/03* (2006.01)

(52) U.S. Cl.
CPC .......... *A61B 6/0492* (2013.01); *A61N 5/1069* (2013.01); *G06T 7/13* (2017.01); *G06T 7/337* (2017.01); *G06T 7/37* (2017.01); *G06T 7/70* (2017.01); *G06T 7/73* (2017.01); *A61B 6/0421* (2013.01); *G06T 2207/10048* (2013.01); *G06T 2207/10072* (2013.01); *G06T 2207/30201* (2013.01); *G06T 2207/30204* (2013.01)

(56) References Cited

U.S. PATENT DOCUMENTS

| | | | | |
|---|---|---|---|---|
| 7,889,906 B2* | 2/2011 | Smith | ............... | G06T 17/205 382/132 |
| 8,155,416 B2* | 4/2012 | Nields | ............... | G06T 7/33 382/131 |
| 8,790,281 B2* | 7/2014 | Diederich | ............... | A61N 7/022 601/3 |
| 9,486,170 B2* | 11/2016 | Andrews | ............... | A61B 6/032 |
| 2005/0026735 A1* | 2/2005 | Tiesler | ............... | F16H 3/66 475/269 |
| 2006/0182326 A1* | 8/2006 | Schildkraut | ............... | A61N 5/1049 382/132 |
| 2008/0002811 A1* | 1/2008 | Allison | ............... | A61N 5/1049 378/65 |
| 2008/0109013 A1* | 5/2008 | Fu | ............... | A61B 6/4458 606/130 |
| 2008/0240353 A1* | 10/2008 | Myles | ............... | G16H 50/50 378/65 |
| 2009/0018711 A1* | 1/2009 | Ueda | ............... | G08G 1/167 701/1 |
| 2009/0316965 A1* | 12/2009 | Mailling | ............... | A43D 1/025 382/128 |
| 2013/0287167 A1* | 10/2013 | Gum | ............... | G06T 7/0016 378/20 |
| 2015/0265852 A1* | 9/2015 | Meir | ............... | A61N 5/1069 600/1 |
| 2015/0302608 A1* | 10/2015 | Vilsmeier | ............... | G06T 7/251 382/131 |
| 2018/0193667 A1* | 7/2018 | Kaiser | ............... | A61B 5/0035 |
| 2018/0272153 A1* | 9/2018 | Berlinger | ............... | A61N 5/107 |
| 2019/0156497 A1* | 5/2019 | Berlinger | ............... | G06T 7/33 |
| 2019/0254564 A1* | 8/2019 | Schwartz | ............... | A61B 34/10 |

FOREIGN PATENT DOCUMENTS

| | | |
|---|---|---|
| WO | 2014057280 A1 | 4/2014 |
| WO | 2015120906 A1 | 8/2015 |

OTHER PUBLICATIONS

Mark H. Philips, PhD. et al., "Commissioning an Image-Guided Localization System for Radiotherapy", Int. J. Radiation Oncology Biol. Phys., vol. 48, No. 1, Aug. 1, 2000, pp. 267-276.

Kamath R. et al., "Initial Clinical Experience with Frameless Radiosurgery for Patients with Intracranial Metastases", International Journal of Radiation: Oncology Biology Physics, Pergamon Press, USA, vol. 61, No. 5, pp. 1467-1472.

Baur, et al., "Multi-modal Surface Registration for Markerless Initial Patient Setup in Radiation Therapy usinig Microsoft's Kinect Sensor", Computer Vision Workshops (ICCV Workshops), 2011 IEEE International Conference on IEEE, 2011, pp. 1-7.

European Patent Office, International Search Report and Written Opinion corresponding to PCT/EP2016/060048, dated Feb. 6, 2017, pp. 1-12.

* cited by examiner

Approach 1:
Fixed Image: (Real) Live Thermal Image
Moving Image: Simulated Thermal Image (starting from reference position)

Approach 2:
Fixed Image: Simulated Thermal Image
Moving Image: (Real) Live Thermal Image (starting from initial couch/patient position)

PATIENT PRE-POSITIONING IN FRAMELESS CRANIAL RADIOSURGERY USING THERMAL IMAGING

RELATED APPLICATION DATA

This application is a National Phase Application of International Application No. PCT/EP2016/060048 filed May 4, 2016, published in the English language.

The present invention relates to a computer-implemented method for supporting positioning a patient for treatment by at least one of radiotherapy or radiosurgery, a corresponding computer program, a non-transitory program storage medium storing such a program and a computer for executing the program, as well as a system for supporting positioning a patient for treatment by at least one of radiotherapy or radiosurgery, the system comprising an electronic data storage device and the aforementioned computer.

TECHNICAL BACKGROUND

In radiotherapy and radiosurgery it is of great importance to have reliable information about the correct placement of the patient (specifically, the target to be irradiated with a treatment beam) relative to the beam source. For example, the patient needs to be correctly pre-positioned on the treatment couch so that any finer positioning algorithm will have a good start point for successful execution of the positioning algorithm. Previous approaches to pre-positioning include determination of the patient's position by detecting reflecting markers fixedly attached to the patient's body in a known spatial relationship. Such, however, requires the markers to be kept clean during the positioning procedure and requires a further step to the pre-positioning procedure which involves attaching the markers.

The present invention is designed render a pre-positioning procedure for radiotherapy or radiosurgery more efficient.

The present invention can be used in connection with a system for image-guided radiotherapy such as ExacTrac®, a product of Brainlab AG.

Aspects of the present invention, examples and exemplary steps and their embodiments are disclosed in the following. Different exemplary features of the invention can be combined in accordance with the invention wherever technically expedient and feasible.

Exemplary Short Description of the Present Invention

In the following, a short description of the specific features of the present invention is given which shall not be understood to limit the invention only to the features or a combination of the features described in this section.

The disclosed method encompasses comparing a live thermal image (infrared image) of a reference structure having a known position relative to an anatomical body part of a patient to a predetermined medical image of the reference structure associated with a known position relative to a reference position such as a radiotherapy isocentre. On that basis, it is determined whether the reference structure has moved relative to the reference position. The aim of the method is to check whether the reference structure and therefore the patient has been correctly positioned and/or kept his desired position relative to a treatment device, and to compensate any possible positional deviation by moving e.g. the patient.

General Description of the Present Invention

In this section, a description of the general features of the present invention is given for example by referring to possible embodiments of the invention.

In general, the invention reaches the aforementioned object by providing, in a first aspect, a computer-implemented method for supporting positioning (for example, pre-positioning or monitoring the position of) a patient for treatment by at least one of radiotherapy or radiosurgery. The method comprises executing, on at least one processor of at least one computer, the following exemplary steps which are executed by the at least one processor.

In a (for example first) exemplary step, planning image data is acquired which describes (for example, defines or represents) a digital planning image of a reference structure. For example, the reference structure comprises (for example, is) at least one of a medical device (such as at least one of a part of a patient support unit on which the patient is placed for the at least one of radiotherapy or radiosurgery (for example, cranial radiotherapy or radiosurgery), or a face mask for attaching to the patient's face e.g. for localizing the patient in space) or an anatomical body part (such as a part of the patient's face, for example on the surface of the face, or a part of the patient's torso). The planning image data has been generated with at least one of different medical imaging modalities such as computed x-ray tomography (CT), magnetic resonance tomography (MRT), ultrasound tomography or thermal (infrared) imaging. For example, the planning image data has been generated by applying a tomographic imaging modality (e.g. CT, MRT or ultrasound) to the reference structure, or by imaging the reference structure with an infrared-sensitive imaging device. The step of generating the planning image data is not necessarily part of the disclosed method, but may under circumstances be part of the disclosed method. In one example, the planning image data has been generated before execution of the disclosed method starts so that the planning image data is predetermined and merely used as an input to the disclosed method. For example, the planning image is taken before the patient is placed ready (pre-positioned) for the at least one of radiotherapy or radiosurgery.

In a further (for example second) exemplary step, reference structure position data is acquired which describes (for example defines or represents) a predetermined (for example at least one of known or fixed) relative position between the reference structure and an anatomical body part of the patient's body and describing a relative position between the reference structure and a predetermined (for example, known and specifically, fixed) reference position. The predetermined reference position was for example known from the imaging geometry (i.e. at least the relative position between an imaging device used for taking the planning image and the imaged reference structure) at the time at which the planning image data was generated and/or the planning image was taken. The anatomical body part may be any part of the patient's body, and if the reference structure is an anatomical body part, the anatomical body part and the reference structure may be at least substantially the same and/or identical. The predetermined reference position is in one example the isocentre of a treatment device usable for treating the patient with the at least one of radiotherapy or radiosurgery.

In a further (for example third) exemplary step, thermal image data is acquired which describes (for example, defines or represents) a digital thermal image (i.e. an infrared image) of the reference structure. For example, the thermal image is taken after the patient has been placed ready (pre-positioned) for the at least one of radiotherapy or radiosurgery (for example on a patient support unit such as a couch of a treatment device for carrying out the at least one of radiotherapy or radiosurgery). Thus, generation of the thermal image data is in one example part of the disclosed method.

In a further (for example fourth) exemplary step, imaging device position data is acquired which describes (for example, defines or represents) a relative position between the reference structure and a thermal imaging device (for example, an infrared camera, specifically, a stereo-camera sensitive in the infrared wavelength range) used for taking the digital thermal image and describing a predetermined (for example, at least one of known or fixed) relative position between the thermal imaging device and the predetermined reference position. That predetermined relative position may describe (for example, define or represent) at least one of the distance and the (for example three-dimensional) orientation and/or perspective from the thermal imaging device (specifically, from the position of the thermal imaging device) to the predetermined reference position.

In a further (for example fifth) exemplary step, planning image pattern data is determined which describes (for example, defines or represents) an image pattern (such as a at least one of a contour or planar area) in the digital planning image assigned to (for example, being) the representation of the reference structure, hereinforth called planning image pattern. The planning image data is determined for example based on (for example, from) the planning image data. For example, determining the planning image pattern data comprises segmentation of the representation of the reference structure in the digital planning image. Thereby, for example a contour (e.g. the circumference) of at least part of the reference structure or an area describing the reference structure in the planning image can be determined.

In a further (for example sixth) exemplary step, thermal image pattern data is determined which describes (for example, defines or represents) an image pattern (such as at least one of a contour or planar area) in the digital thermal image assigned to (for example, being) the representation of the reference structure, hereinforth called thermal image pattern. The thermal image pattern data is determined for example based on (for example, from) the thermal image data. For example, determining the thermal image pattern data comprises segmentation of the representation of the reference structure in the thermal image. Thereby, for example a contour (e.g. the circumference) of at least part of the reference structure or an area describing the reference structure in the thermal image can be determined. For example, the thermal image pattern is an infrared signature of the reference structure.

In examples of the for example fifth and sixth exemplary steps, determining the planning image data and the thermal image pattern data comprises determining similarity measure data (for example, by comparing the planning image to the thermal image) describing a similarity measure (such as a normalized cross-correlation, or image unit-wise (e.g. pixel-wise or voxel-wise) difference image and/or sum of squared differences) defining a similarity between image features in the digital planning image and the digital thermal image. Image features associated with a high similarity measure can be (for example, are) considered to comprise (for example, be) the representation of the reference structure in the respective image. In case the planning image and the thermal image have different dimensions, at least one of them may be stretched for example by interpolation of image unit values (pixel values or voxel values) in the images so as to match the image dimensions with one another for comparing them to determine the similarity measure.

In a further (for example seventh) exemplary step, positional difference data is determined which describes (for example defines or represents) a difference between a relative position between the anatomical body part and the predetermined reference position at the point in time at which planning image data was generated on the one hand, and a relative position between the anatomical body part and the predetermined reference position at the point in time at which the thermal image data was generated on the other hand. The difference may be equal to zero, but may also differ from zero. The positional difference data is determined for example based on (for example, from) the reference structure position data and the imaging device position data and the planning image pattern data and the thermal image pattern data.

In one example of the for example seventh exemplary step, the positional difference data describes a transformation between the relative position between the anatomical body part and the predetermined reference position at the point in time at which planning image data was generated on the one hand, and the relative position between the anatomical body part and the predetermined reference position at the point in time at which the thermal image data was generated on the other hand. Within the meaning of this disclosure, a transformation is understood to be a linear transformation such as a mapping which can be embodied by a mapping matrix (which encompasses a vector) which considers for example at least three spatial degrees of freedom. A transformation can be determined by accordingly solving the associated linear mapping equation, using basic linear algebra.

In another example of the for example seventh exemplary step, determining the positional difference data comprises:
  determining, based on (for example, from) the similarity measure data and the reference structure position data and the imaging device position data, relative position data describing (for example defining or representing) the relative position between the anatomical body part and the predetermined reference position at the point in time at which planning image data was generated on the one hand, and the relative position between the anatomical body part and the predetermined reference position at the point in time at which the thermal image data was generated on the other hand.

In one example of the for example first exemplary step, the disclosed method comprises:
  acquiring, at the at least one processor, thermal reference data describing a predetermined model of a thermal image appearance of the reference structure, and
  determining, by the at least one processor and based on the thermal reference data and the planning image data, thermal planning data describing a mapping of the predetermined model onto the digital planning image,
  wherein the positional difference data is determined based on (e.g. from) the thermal planning data.

The thermal reference data (for example, the predetermined model) is predetermined, i.e. generated before execution of the disclosed method starts, and read as an input to the disclosed method. The predetermined model is generated for example by a statistical analysis of a plurality of thermal images so as to generate for example an average infrared signature of the reference structure for example under standard external conditions. If the reference structure is an anatomical body part, the predetermined model is generated for example by a statistical analysis of thermal images of the corresponding anatomical body part of a suitable plurality of human bodies. The predetermined model may therefore be considered to represent a thermal atlas (thermo-atlas) of the reference structure. The thermal planning data is for example generated by applying an image fusion algorithm to the planning image data and the thermal reference data in order to establish a transformation describing (for example defining or representing) the mapping of the predetermined model onto the digital planning image, specifically of corresponding image features in the predetermined model and the digital planning image onto each other. Thereby, the representation of the reference structure in the predetermined model is mapped onto (for example matched with) the representation of the reference structure in the planning image. In doing so, for example a re-shaped predetermined model conforming to the shape of the representation of the reference structure in the planning image can be generated. The re-shaped predetermined model can then be compared to the representation of the reference structure in the thermal image, for example by applying an image fusion algorithm to the thermal image data and re-shaped thermal reference data (or the thermal planning data and the thermal reference data) so as to determine the position of the representation of the reference structure in the thermal image. Alternatively, the position of the representation of the reference structure in the thermal image may be determined by the ways of determining the similarity measure as described above in the context of the for example fourth and fifth exemplary steps, namely by determining a similarity measure between the re-shaped predetermined model and the thermal image.

Alternatively, the thermal reference data can have been generated for example by imaging the reference structure with a non-thermal imaging modality (e.g. with CT or MRT) and assigning current or predetermined temperature values to the reference structure. For example, if the reference structure is a medical device which is for example attached to the patient (for example, a face mask), the reference structure can be imaged in a state in which it is attached to the patient. In the resulting image, the representation of the reference structure can be segmented (i.e. determined by contour analysis), and different temperature values can be assigned to the representation of the reference structure and the representation of an anatomical body part of the patient (e.g. parts of the face which are visible through the mask). For example, the reference structure can be assigned lower temperature values than the anatomical body part. This results in creation of an artificial (simulated) thermal image of the reference structure, the planning image pattern then being defined by the contour of the representation of the reference structure in the artificial thermal image or by the area in the artificial thermal image occupied by the representation of the reference structure. The positional difference data can then be determined by comparing the artificial thermal image to the thermal image described by the thermal image data, for example by image unit-wise comparison.

In a further example, the disclosed method comprises a step of determining, based on (e.g. from) the positional difference data, treatment device control data describing (for example, defining or representing) positional control information for controlling a relative position between a patient support unit for supporting the patient's body and a treatment device usable for treating the patient with at least one of radiotherapy or radiosurgery (for example, by moving at least one of the patient support unit or another part of the treatment device such as a beam source using a motorized motion control unit). For example, control data describing (for example, defining or representing) a command for moving the patient support unit relative to the treatment device is determined based on the treatment device control data. The command can be issued to the motion control unit. For example, the relative position between the patient support unit and the treatment device is changed such that a target area being the target of the at least one of radiotherapy or radiosurgery is positioned at a predetermined position such as the reference position. Alternatively or additionally, the control data may describer (for example, define or represent) a command for controlling a beam source of the treatment device, for example to switch on or switch of a treatment beam or generally change the intensity of a treatment device.

In a second aspect, the invention is directed to a computer program which, when running on at least one processor (for example, a processor) of at least one computer (for example, a computer) or when loaded into at least one memory (for example, a memory) of at least one computer (for example, a computer), causes the at least one computer to perform the above-described method according to the first aspect.

In a third aspect, the invention is directed to a non-transitory computer-readable program storage medium on which the program according to the second aspect is stored.

In a fourth aspect, the invention is directed to at least one computer (for example, a computer), comprising at least one processor (for example, a processor) and at least one memory (for example, a memory), wherein the program according to the second aspect is running on the processor or is loaded into the memory, or wherein the at least one computer comprises the program storage medium according to the third aspect.

In a fifth aspect, the invention is directed to a system for supporting positioning a patient for treatment by at least one of radiotherapy or radiosurgery, the system comprising:
  a) the at least one computer according to the fourth aspect;
  b) at least one electronic data storage device storing at least the planning image data, the reference structure position data and the imaging device position data;
  c) a thermal imaging device for taking the digital thermal image, the thermal imaging device being operably coupled to the at least one computer for transmitting a signal to the at least one computer corresponding to the thermal image data;
  d) a treatment device usable for treating the patient with at least one of radiotherapy or radiosurgery; and
  e) a patient support unit (for example, a couch) for supporting the patient's body.

The at least one computer is operably coupled to the at least one electronic data storage device for acquiring, from the at least one data storage device, the planning image data, the reference structure position data and the imaging device position data. Furthermore, the computer is operably coupled to at least one of the treatment device or the patient support unit.

It is within the scope of the present invention to combine one or more features of one or more embodiments or aspects of the invention in order to form a new embodiment wherever this is technically expedient and/or feasible. Specifically, a feature of one embodiment which has the same or a similar function to another feature of another embodiment can be exchanged with said other feature, and a feature of one embodiment which adds an additional function to another embodiment can for example be added to said other embodiment.

Definitions

In this section, definitions for specific terminology used in this disclosure are offered which also form part of the present disclosure.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

The method in accordance with the invention is for example a computer implemented method. For example, all the steps or merely some of the steps (i.e. less than the total number of steps) of the method in accordance with the invention can be executed by a computer (for example, at least one computer). An embodiment of the computer implemented method is a use of the computer for performing a data processing method. An embodiment of the computer implemented method is a method concerning the operation of the computer such that the computer is operated to perform one, more or all steps of the method.

The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is an augmented reality device (also referred to as augmented reality glasses) which can be used as "goggles" for navigating. A specific example of such augmented reality glasses is Google Glass (a trademark of Google, Inc.). An augmented reality device can be used both to input information into the computer by user interaction and to display information outputted by the computer.

Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. The monitor may also be the monitor of a portable, for example handheld, device such as a smart phone or personal digital assistant or digital media player.

The expression "acquiring data" for example encompasses (within the framework of a computer implemented method) the scenario in which the data are determined by the computer implemented method or program. Determining data for example encompasses measuring physical quantities and transforming the measured values into data, for example digital data, and/or computing the data by means of a computer and for example within the framework of the method in accordance with the invention. The meaning of "acquiring data" also for example encompasses the scenario in which the data are received or retrieved by the computer implemented method or program, for example from another program, a previous method step or a data storage medium, for example for further processing by the computer implemented method or program. Generation of the data to be acquired may but need not be part of the method in accordance with the invention. The expression "acquiring data" can therefore also for example mean waiting to receive data and/or receiving the data. The received data can for example be inputted via an interface. The expression "acquiring data" can also mean that the computer implemented method or program performs steps in order to (actively) receive or retrieve the data from a data source, for instance a data storage medium (such as for example a ROM, RAM, database, hard drive, etc.), or via the interface (for instance, from another computer or a network). The data acquired by the disclosed method or device, respectively, may be acquired from a database located in a data storage device which is operably to a computer for data transfer between the database and the computer, for example from the database to the computer. The computer acquires the data for use as an input for steps of determining data. The determined data can be output again to the same or another database to be stored for later use. The database or database used for implementing the disclosed method can be located on network data storage device or a network server (for example, a cloud data storage device or a cloud server) or a local data storage device (such as a mass storage device operably connected to at least one computer executing the disclosed method). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

In the field of medicine, imaging methods (also called imaging modalities and/or medical imaging modalities) are used to generate image data (for example, two-dimensional or three-dimensional image data) of anatomical structures (such as soft tissues, bones, organs, etc.) of the human body. The term "medical imaging methods" is understood to mean (advantageously apparatus-based) imaging methods (so-called medical imaging modalities and/or radiological imaging methods) such as for instance computed tomography (CT) and cone beam computed tomography (CBCT, such as volumetric CBCT), x-ray tomography, magnetic resonance tomography (MRT or MRI), conventional x-ray, sonography and/or ultrasound examinations, and positron emission tomography. The image data thus generated is also termed "medical imaging data". Analytical devices for example are used to generate the image data in apparatus-based imaging methods. The imaging methods are for example used for medical diagnostics, to analyse the anatomical body in order to generate images which are described by the image data. The imaging methods are also for example used to detect pathological changes in the human body. However, some of the changes in the anatomical structure, such as the pathological changes in the structures (tissue), may not be detectable and for example may not be visible in the images generated by the imaging methods. A tumour represents an example of a change in an anatomical structure. If the tumour grows, it may then be said to represent an expanded anatomical structure. This expanded anatomical structure may not be detectable; for example, only a part of the expanded anatomical structure may be detectable. Primary/high-grade brain tumours are for example usually visible on MRI scans when contrast agents are used to infiltrate the tumour. MRI scans represent an example of an imaging method. In the case of MRI scans of such brain tumours, the signal enhancement in the MRI images (due to the contrast agents infiltrating the tumour) is considered to represent the solid tumour mass. Thus, the tumour is detectable and for example discernible in the image generated by the imaging method. In addition to these tumours, referred to as "enhancing" tumours, it is thought that approximately 10% of brain tumours are not discernible on a scan and are for example not visible to a user looking at the images generated by the imaging method.

Image fusion can be elastic image fusion or rigid image fusion. In the case of rigid image fusion, the relative position between the pixels of a 2D image and/or voxels of a 3D image is fixed, while in the case of elastic image fusion, the relative positions are allowed to change.

In this application, the term "image morphing" is also used as an alternative to the term "elastic image fusion", but with the same meaning.

Elastic fusion transformations (for example, elastic image fusion transformations) are for example designed to enable a seamless transition from one dataset (for example a first dataset such as for example a first image) to another dataset (for example a second dataset such as for example a second image). The transformation is for example designed such that one of the first and second datasets (images) is deformed, for example in such a way that corresponding structures (for example, corresponding image elements) are arranged at the same position as in the other of the first and second images. The deformed (transformed) image which is transformed from one of the first and second images is for example as similar as possible to the other of the first and second images. Preferably, (numerical) optimisation algorithms are applied in order to find the transformation which results in an optimum degree of similarity. The degree of similarity is preferably measured by way of a measure of similarity (also referred to in the following as a "similarity measure"). The parameters of the optimisation algorithm are for example vectors of a deformation field. These vectors are determined by the optimisation algorithm in such a way as to result in an optimum degree of similarity. Thus, the optimum degree of similarity represents a condition, for example a constraint, for the optimisation algorithm. The bases of the vectors lie for example at voxel positions of one of the first and second images which is to be transformed, and the tips of the vectors lie at the corresponding voxel positions in the transformed image. A plurality of these vectors is preferably provided, for instance more than twenty or a hundred or a thousand or ten thousand, etc. Preferably, there are (other) constraints on the transformation (deformation), for example in order to avoid pathological deformations (for instance, all the voxels being shifted to the same position by the transformation). These constraints include for example the constraint that the transformation is regular, which for example means that a Jacobian determinant calculated from a matrix of the deformation field (for example, the vector field) is larger than zero, and also the constraint that the transformed (deformed) image is not self-intersecting and for example that the transformed (deformed) image does not comprise faults and/or ruptures. The constraints include for example the constraint that if a regular grid is transformed simultaneously with the image and in a corresponding manner, the grid is not allowed to interfold at any of its locations. The optimising problem is for example solved iteratively, for example by means of an optimisation algorithm which is for example a first-order optimisation algorithm, such as a gradient descent algorithm. Other examples of optimisation algorithms include optimisation algorithms which do not use derivations, such as the downhill simplex algorithm, or algorithms which use higher-order derivatives such as Newton-like algorithms. The optimisation algorithm preferably performs a local optimisation. If there is a plurality of local optima, global algorithms such as simulated annealing or generic algorithms can be used. In the case of linear optimisation problems, the simplex method can for instance be used.

In the steps of the optimisation algorithms, the voxels are for example shifted by a magnitude in a direction such that the degree of similarity is increased. This magnitude is preferably less than a predefined limit, for instance less than one tenth or one hundredth or one thousandth of the diameter of the image, and for example about equal to or less than the distance between neighbouring voxels. Large deformations can be implemented, for example due to a high number of (iteration) steps.

The determined elastic fusion transformation can for example be used to determine a degree of similarity (or similarity measure, see above) between the first and second datasets (first and second images). To this end, the deviation between the elastic fusion transformation and an identity transformation is determined. The degree of deviation can for instance be calculated by determining the difference between the determinant of the elastic fusion transformation and the identity transformation. The higher the deviation, the lower the similarity, hence the degree of deviation can be used to determine a measure of similarity.

A measure of similarity can for example be determined on the basis of a determined correlation between the first and second datasets.

The present invention relates to the field of controlling a treatment beam. The treatment beam treats body parts which are to be treated and which are referred to in the following as "treatment body parts". These body parts are for example parts of a patient's body, i.e. anatomical body parts.

The present invention relates to the field of medicine and for example to the use of beams, such as radiation beams, to treat parts of a patient's body, which are therefore also referred to as treatment beams. A treatment beam treats body parts which are to be treated and which are referred to in the following as "treatment body parts". These body parts are for example parts of a patient's body, i.e. anatomical body parts. Ionising radiation is for example used for the purpose of treatment. For example, the treatment beam comprises or consists of ionising radiation. The ionising radiation comprises or consists of particles (for example, sub-atomic particles or ions) or electromagnetic waves which are energetic enough to detach electrons from atoms or molecules and so ionise them. Examples of such ionising radiation include x-rays, high-energy particles (high-energy particle beams) and/or ionising radiation emitted from a radioactive element. The treatment radiation, for example the treatment beam, is for example used in radiation therapy or radiotherapy, such as in the field of oncology. For treating cancer in particular, parts of the body comprising a pathological structure or tissue such as a tumour are treated using ionising radiation. The tumour is then an example of a treatment body part.

The treatment beam is preferably controlled such that it passes through the treatment body part. However, the treatment beam can have a negative effect on body parts outside the treatment body part. These body parts are referred to here as "outside body parts". Generally, a treatment beam has to pass through outside body parts in order to reach and so pass through the treatment body part.

DESCRIPTION OF THE FIGURES

In the following, the invention is described with reference to the appended figures which represent a specific embodiment of the invention. The scope of the invention is however not limited to the specific features disclosed in the context of the figures, wherein

FIG. 1 is a flow diagram illustrating the basic steps of the disclosed method which in the illustrative example of FIG. 1 starts with a step S1 of acquiring the planning image data. In subsequent step S2, the reference structure position data is acquired, followed by step S3 which is directed to acquiring the thermal image data. Then, step S4 continues with acquiring the imaging device position data. This is followed by step S5 which encompasses determining the planning image pattern data, and by step S6 which encompasses determining the thermal image pattern data. In step S7 which is illustrated in FIG. 1 as the final method step, the positional difference data is determined.

FIG. 2a is a photograph of a patient wearing an open face mask, and a thermal image corresponding to this photograph is shown in FIG. 2b. The temperature of the visible ("open") portion of the face is approximately 37° C. which is significantly higher than that of the mask which is approximately 20° C. (room temperature). The patient is lying on the treatment couch, but as treatment couch and mask do have room temperature, only the open face becomes apparent in FIG. 2b. The patient is wearing the mask already during the scanning process for generating the planning image data. Based on the planning image, the treatment is planned and the target position (isocentre) is determined.

FIG. 3a shows a segmentation of the mask in the CT data corresponding to the planning image data for determining which image constituent corresponds to the mask and which image constituent corresponds to the patient's face. As shown in FIG. 3b, a thermal image of the patient wearing the mask can also be taken from a different perspective.

Therefore it is possible to assign a low temperature value to voxels representing the mask and high temperature values to voxels representing the face. The thereby created volume is in the following called thermal volume. Thus, a simulated thermal image (which can be a binary thermal image representing the silhouette of the face) can be rendered from the thermal volume. Having the calibration to the treatment device isocentre (represented by a projection matrix) of the thermal camera, and knowing that the treatment isocentre is defined in the volume data (CT data), an exact reference image for pre-positioning the patient can be rendered. The treatment couch can then be iteratively driven into the isocentre position so that the resulting live thermal image matches the simulated thermal image. Alternatively, the position of the thermal volume is virtually optimized in space so that the resulting simulated thermal image matches the thermal image (live thermal image) described by the thermal image data. The transformation resulting therefrom is used for pre-positioning.

Figure 1:
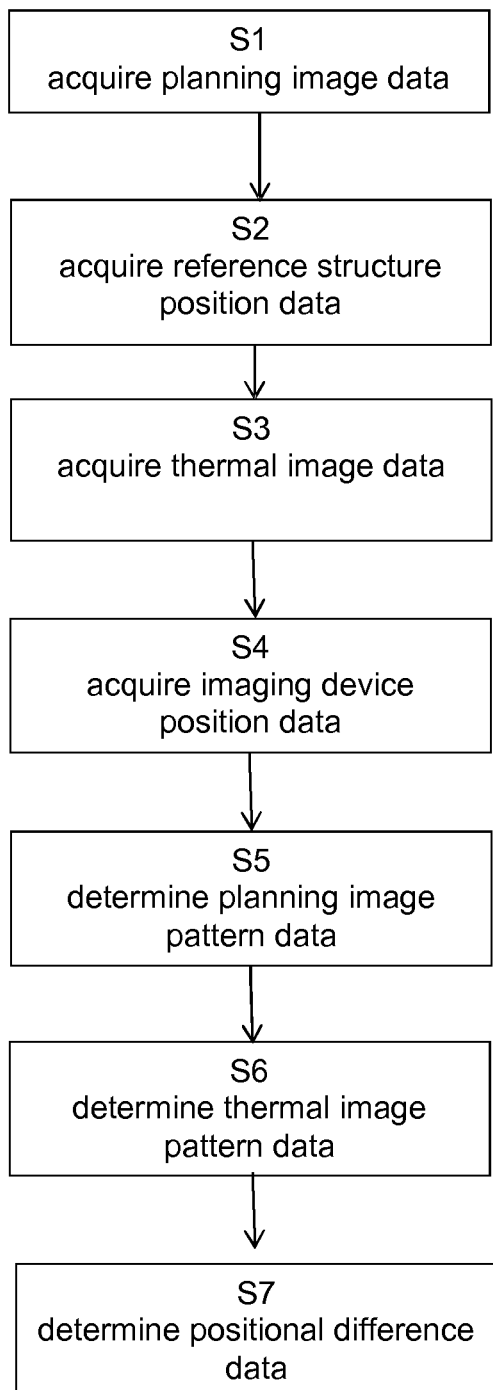
FIG. 1 is a flow diagram showing the basic steps of the disclosed method.
Figure 2A:
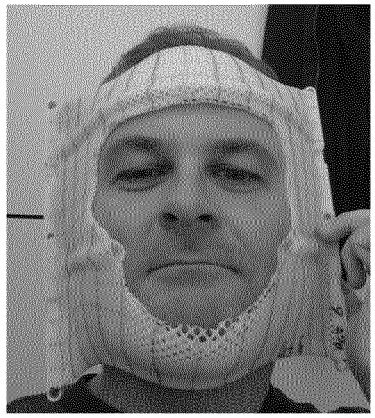
FIG. 2a shows a face mask attached to a patient.
Figure 2B:
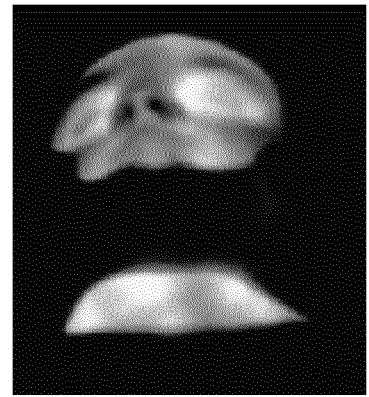
FIG. 2b shows the infrared signature of the patient's face with the face mask attached to the face.
Figure 3A:
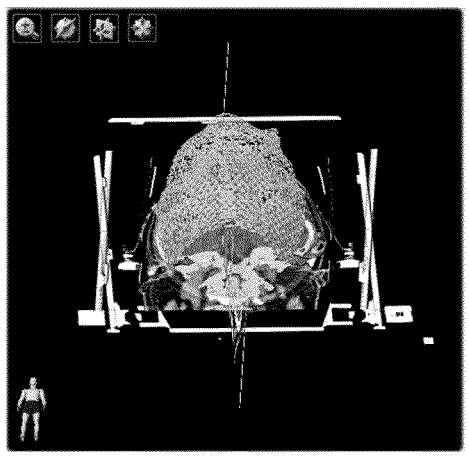
FIG. 3a illustrates a CT scan with a segmentation of the face mask.
Figure 3B:
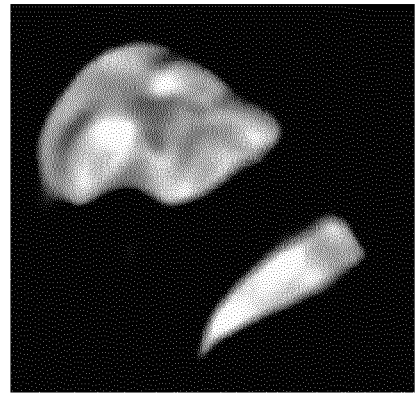
FIG. 3b illustrates the infrared signature of FIG. 2b after the couch has been moved.
Figure 4:
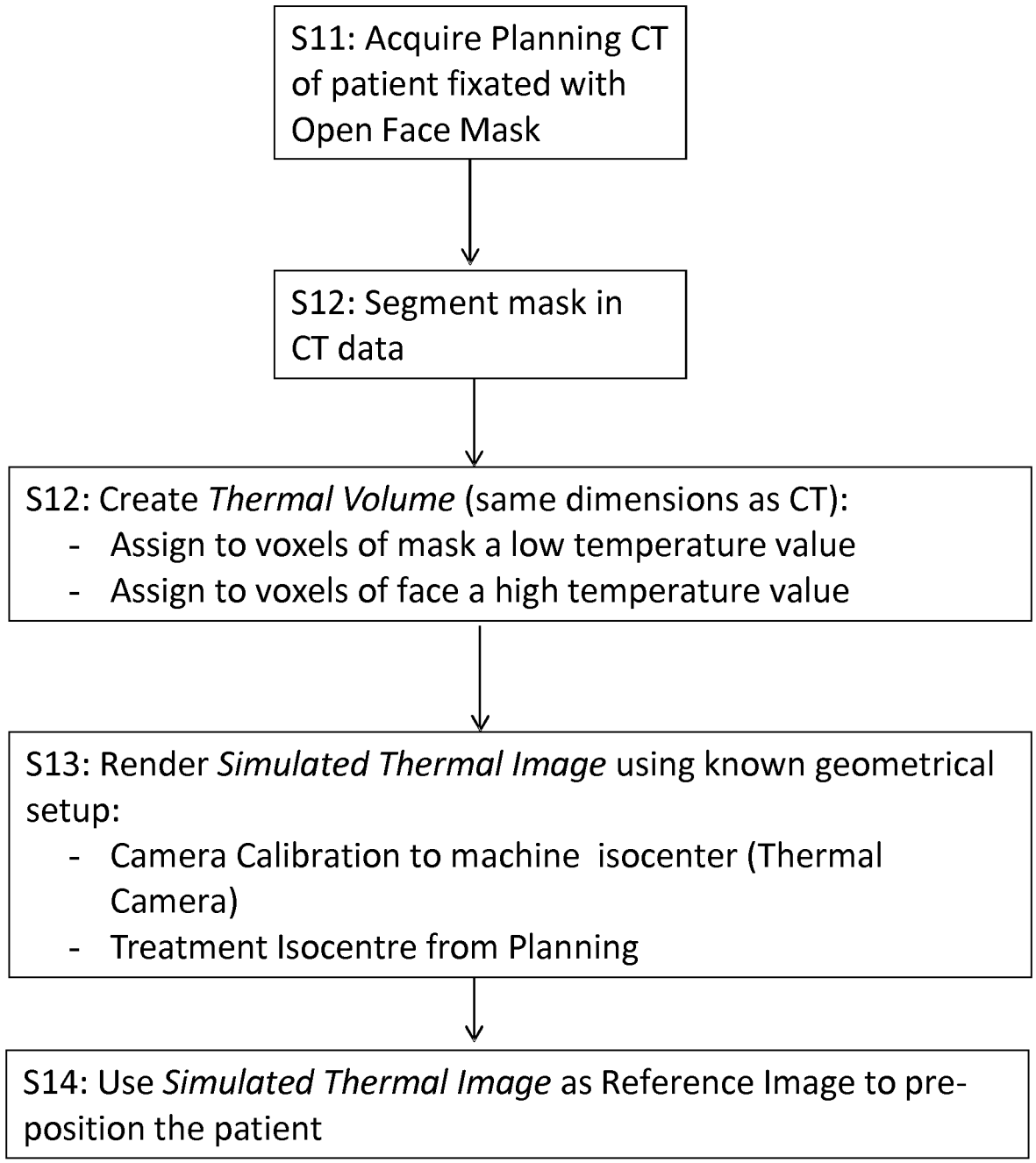
FIG. 4 shows as an embodiment of the algorithm illustrated in FIG. 1.

FIG. 4 shows an embodiment of the algorithm shown in FIG. 1. Initial step S11 encompasses acquisition of the planning CT embodying the planning image of the patient to whose face an open face mask is fixated. In subsequent step S12, the representation of the mask is segmented in the planning image (CT data). Then, a thermal volume (having the same dimensions as the planning image) is created in step S12 by assigning to voxels of the mask a low temperature, and to voxels of the face a high temperature value. Subsequently, a simulated thermal image is rendered in step S13 using the known geometrical setup of the camera calibration to the machine isocentre for the thermal camera (represented by the imaging device position data) and information about the treatment isocentre already known from the planning image data. The simulated thermal image is rendered in an appearance it would have if the thermal volume were at a desired (planned) position. In the following step S14, the simulated thermal image is used as a reference image to pre-position the patient.

Figure 5:
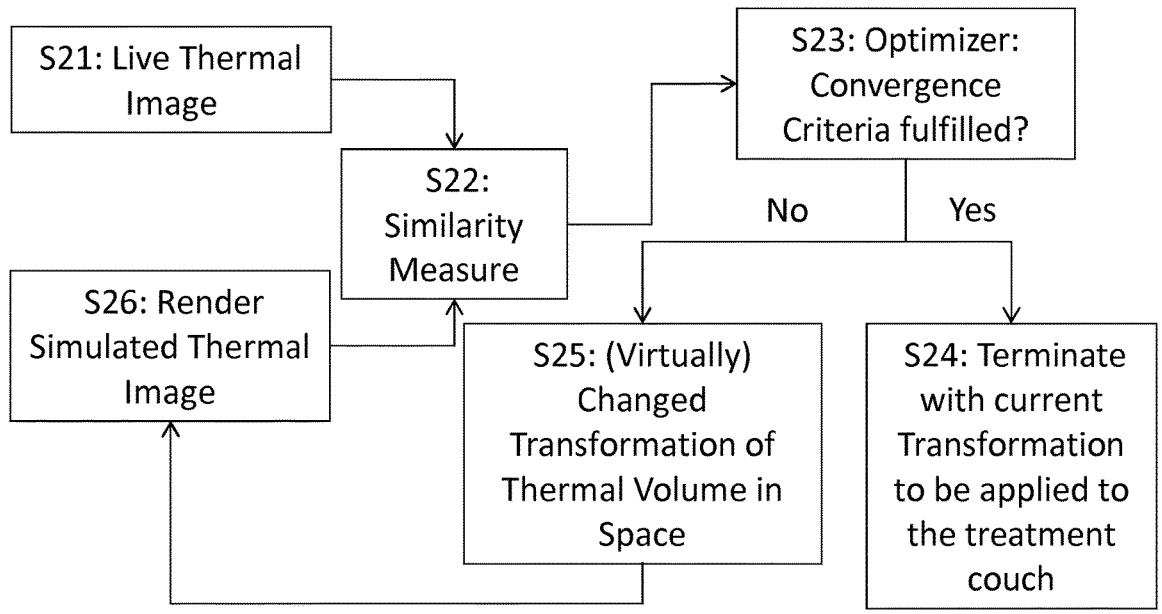
FIG. 5 illustrates a flow diagram for a first approach of computing the positional difference data by image registration when the simulated thermal image is the moving image.

FIG. 5 illustrates an algorithm for generating the similarity measure if the thermal image described by the thermal image data is considered to be at a certain position, and the thermal volume is virtually transformed in space from the desired (planned) position to match that certain position. In step S21 the live thermal image (i.e. the thermal image described by the thermal image data) is acquired and in step S26, the rendered simulated thermal image is acquired. In step S22, the live thermal image and the simulated thermal image are compared to determine the similarity measure. Then, step S23 continues determining whether the similarity measure fulfils a predetermined convergence criterion. If this is the case, step S24 terminates the procedure with the transformation thus determined describing the difference defined by the positional difference data. This transformation is applied to the treatment couch to appropriately move the patient into position. If step S23 determines that the convergence criterion is not fulfilled, the thermal volume is virtually transformed in space to render a new simulated thermal image (from the thermal volume) in step S26, and the procedure continues again with step S22.

Figure 6:
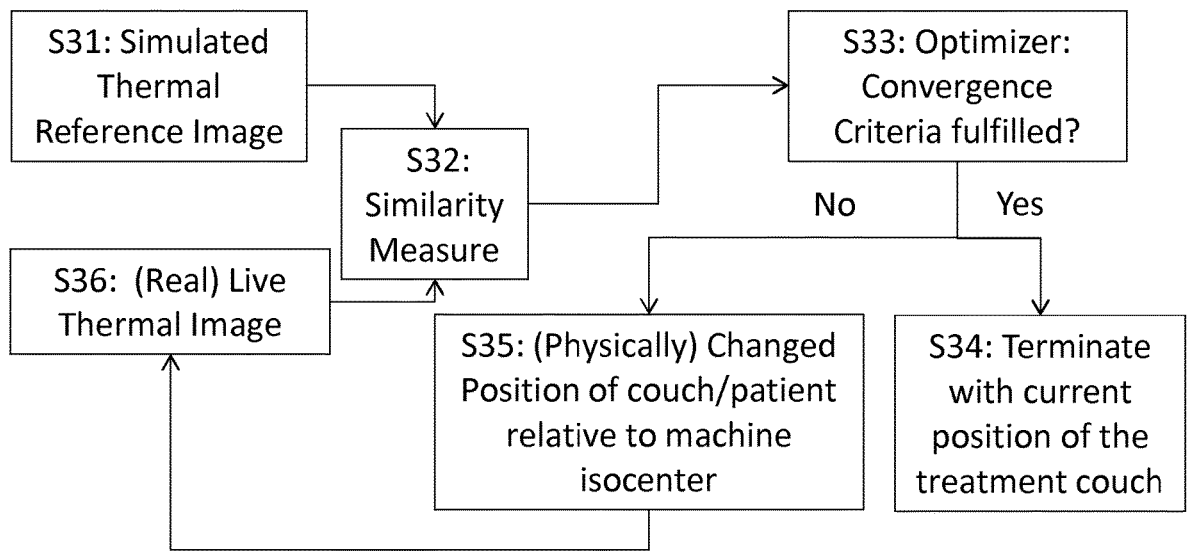
FIG. 6 illustrates a flow diagram for a first approach of computing the positional difference data by image registration when the live thermal image is the moving image.

FIG. 6 shows the case in which the simulated thermal image is considered to be associated with a fixed position, and the live thermal image is considered to be moving. In initial step S31, the simulated thermal image is acquired as a reference image in an appearance it would have if the thermal volume were at a desired (planned) position, and compared in step S32 with the live thermal image acquired in step S36 to determine the similarity measure between the two images. Then, step S33 continues with determining whether the similarity measure fulfils a predetermined convergence criterion. If it is determined that this is the case, step S34 terminates the procedure with the current position of the treatment couch. If step S33 determines that the convergence criterion is not fulfilled, the position of the couch (and the patient) relative to the machine isocentre is physically changed, and a new real live thermal image is acquired in step S36.

Figure 7:
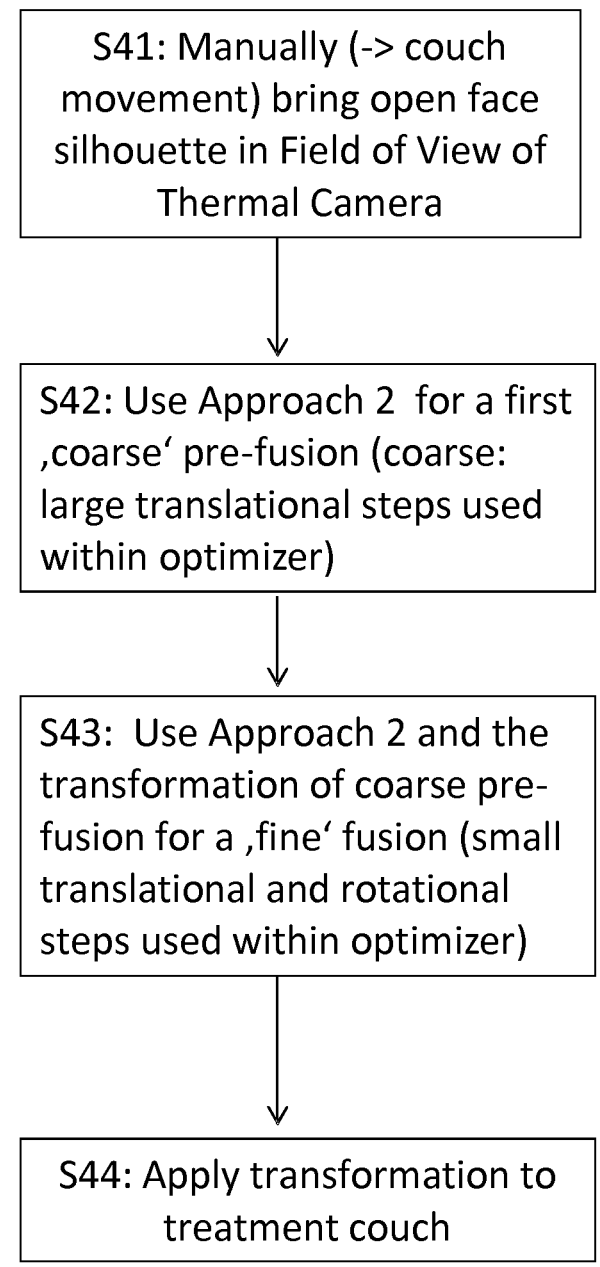
FIG. 7 shows an implementation of the second approach.

FIG. 7 shows an implementation of the second approach shown in FIG. 6. In initial step S41, the open face silhouette of the patient with the face mask attached to his face is manually brought into the field of view of the thermal camera by couch movement. Then, approach to (the second approach) is executed in step S42 for a first (coarse) pre-fusion by applying large translational steps used within the optimizer applied in step S33. This process is repeated in step S43 using smaller translational and rotational steps within the optimizer for a fine fusion. Then, the resulting transformation is applied to the treatment couch in step S44 to appropriately position the patient.

Figure 8:
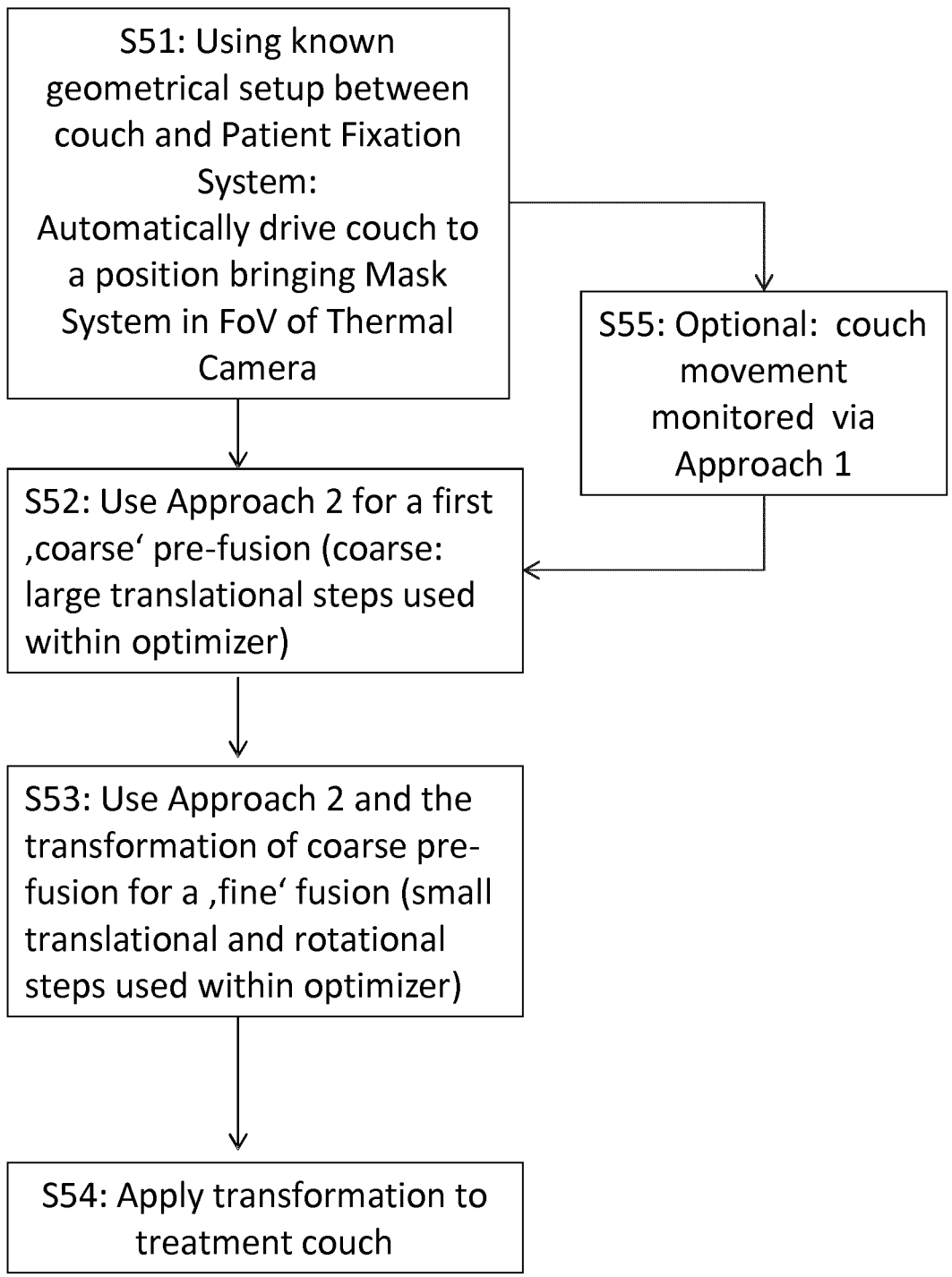
FIG. 8 shows a fully automatic implementation of a pre-positioning procedure using the disclosed method.

FIG. 8 shows the overall flow of a pre-positioning procedure using the method disclosed herein. In step S51 the known geometrical setup between the couch and the patient fixation system for fixing the patient on the couch is used to automatically drive the couch to a position at which the mask (mask system) is brought into the field of view (FoV) of the thermal camera. This is followed by step S52 which encompasses using the second approach (approach 2) for a first coarse pre-fusion (using large translational steps within the optimizer of step S33). This is repeated in step S53 in order to generate a fine fusion using small translational and rotational steps within the optimizer of step S33. The resulting transformation is applied to the treatment couch in step S54 to appropriately position the patient. In optional step S55, the couch movement can be monitored by applying the first approach (approach 1) between execution of step S51 and S52.

Figure 9:
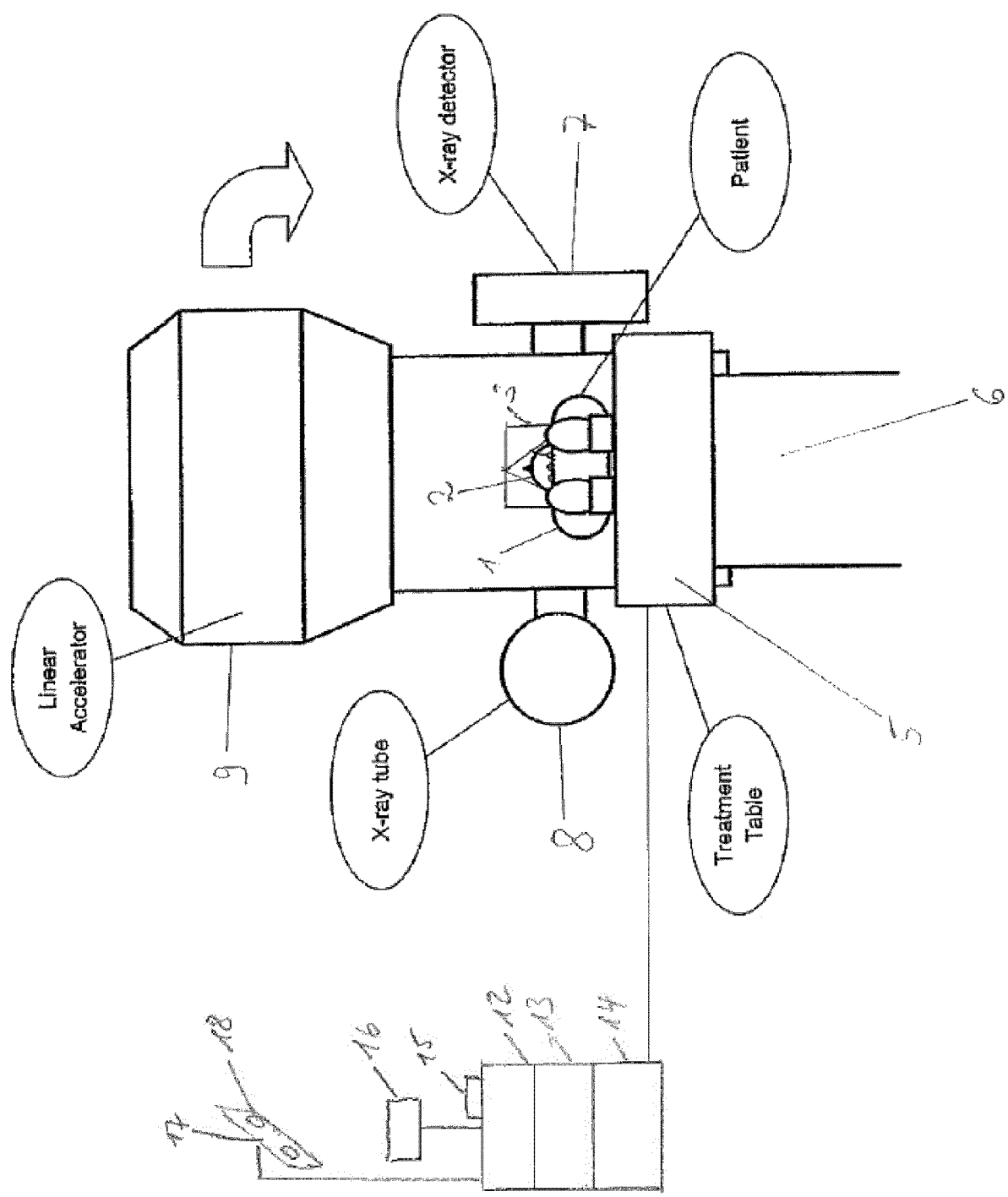
FIG. 9 illustrates the system for use with the disclosed method.

FIG. 9 shows a system for executing the method disclosed herein. The system comprises a computer having a processor 12 and a volatile memory (RAM) 13 which are operably coupled to a non-volatile memory 14 being an electronic data storage device (such as a hard disk) storing at least the planning image data, the reference structure position data and the imaging device position data. The computer is also coupled to an input device (such as at least one of a keyboard or a pointing device like a mouse) 15 and a display device 16 which can be embodied by a monitor. Furthermore, the computer is operably coupled to the thermal imaging device 20 embodied by a thermal camera (an infrared-sensitive camera) 17 having two optical units 18 for taking the digital thermal image described by the thermal image data. The computer is also operably coupled to at least one of a treatment device 9 being a linear accelerator having a beam source for emitting an ionizing treatment beam which has a specifiable position relative to a patient support unit embodied by a couch 5 on which the patient's body 1 is positioned. A reference structure represented by an open face mask 3 is attached to the patient's face 2. The treatment device further may comprise an x-ray tube 8 and an x-ray detector 7 for taking x-ray images for checking the patient's position during the treatment. The computer may alternatively or additionally be operably coupled to a motion control unit embodied by a motor 6 for driving the couch 5 (treatment table) to a desired position relative to the beam source.

The invention claimed is:

1. A computer-implemented medical data processing method for supporting positioning an associated patient for treatment by at least one of radiotherapy or radiosurgery, the method comprising executing, on at least one processor of at least one computer, steps of:
acquiring at the at least one processor, planning image data describing a digital planning image of a reference structure;
acquiring at the at least one processor, reference structure position data describing a predetermined relative position between the reference structure and an anatomical body part of the associated patient and describing a relative position between the reference structure and a predetermined reference position;
acquiring at the at least one processor, thermal image data describing a digital thermal image of the reference structure;
acquiring at the at least one processor, imaging device position data describing a relative position between the reference structure and an associated thermal imaging device used for taking the digital thermal image and describing a predetermined relative position between the associated thermal imaging device and the predetermined reference position;
determining, by the at least one processor and based on the planning image data, planning image pattern data describing a planning image pattern in the digital planning image assigned to a representation of the reference structure;
determining, by the at least one processor and based on the thermal image data, thermal image pattern data describing a thermal image pattern in the digital thermal image assigned to the representation of the reference structure;
determining positional difference data by the at least one processor based on: the reference structure position data, the imaging device position data, the planning image pattern data, and the thermal image pattern data, the positional difference data describing a difference between:
a relative position between the anatomical body part of the associated patient and the predetermined reference position at a point in time at which the planning image data was generated, and
a relative position between the anatomical body part of the associated patient and the predetermined reference position at a point in time at which the thermal image data was generated.

2. The method according to claim 1, wherein the determining the planning image pattern data comprises:
segmenting the representation of the reference structure in the digital planning image.

3. The method according to claim 1, wherein the determining the thermal image pattern data comprises:
segmenting the representation of the reference structure in the digital thermal image.

4. The method according to claim 1, wherein the planning image pattern comprises a contour or an area in the planning image.

5. The method according to claim 1, wherein the thermal image pattern comprises a contour or an area in the planning image.

6. The method according to claim 1, wherein the positional difference data describes a transformation between:
the relative position between the anatomical body part and the predetermined reference position at the point in time at which planning image data was generated; and
the relative position between the anatomical body part and the predetermined reference position at the point in time at which the thermal image data was generated.

7. The method according to claim 1, wherein the predetermined reference position comprises an isocenter of an associated treatment device usable for the radiotherapy or the radiosurgery.

8. The method according to claim 1, wherein the determining the planning image data and the thermal image pattern data comprises:
determining similarity measure data describing a similarity measure defining a similarity between image features in the digital planning image and the digital thermal image.

9. The method according to claim 1, wherein the determining the positional difference data comprises:
determining, by the at least one processor and based on the similarity measure data and the reference structure position data and the imaging device position data, relative position data describing:
the relative position between the anatomical body part and the predetermined reference position at the point in time at which planning image data was generated; and
the relative position between the anatomical body part and the predetermined reference position at the point in time at which the thermal image data was generated.

10. The method according to claim 1, further comprising generating the planning image data by applying a tomographic imaging modality to the reference structure or by imaging the reference structure with an infrared-sensitive imaging device.

11. The method according to claim 1, further comprising:
acquiring, at the at least one processor, thermal reference data describing a predetermined model of a thermal image appearance of the reference structure; and
determining, by the at least one processor and based on the thermal reference data and the planning image data, thermal planning data describing a mapping of the predetermined model onto the digital planning image, wherein the positional difference data is determined based on the thermal planning data.

12. The method according to claim 1, further comprising:
determining, by the at least one processor and based on the positional difference data, treatment device control data describing positional control information for controlling a relative position between a patient support unit for supporting a body of the associated patient and a treatment device usable for treating the patient with at least one of radiotherapy or radiosurgery, and determining, by the at least one processor and based on the treatment device control data, control data describing a command for moving the patient support unit relative to the treatment device and issuing the command to a motion control unit such that a target area being the target of the at least one of radiotherapy or radiosurgery is positioned at the reference position.

13. The method according to claim 1, wherein the acquiring the planning image data describing the digital planning image of the reference structure comprises:
acquiring planning image data describing a digital planning image of:
a face of the associated patient; and
an open face mask medical device attached to the face of the associated patient, the open face mask medical device defining a contour in the planning image data, wherein the planning image pattern data describes the contour as the planning image pattern.

14. The method according to claim 1, wherein the acquiring the thermal image data describing the digital thermal image of the reference structure comprises:
acquiring, after the associated patient has been placed on a patient support unit of a treatment apparatus for carrying out the at least one of the radiotherapy treatment or the radiosurgery, thermal image data describing a digital thermal image of:
the anatomical body part of the associated patient; and
the reference structure attached to the anatomical body part of the associated patient.

15. A non-transitory computer-readable program storage medium storing a program thereon for supporting positioning an associated patient for treatment by at least one of radiotherapy or radiosurgery, the program being executable by a computer of an associated patient pre-positioning apparatus for supporting the pre-positioning by:
acquiring planning image data describing a digital planning image of a reference structure;
acquiring reference structure position data describing a predetermined relative position between the reference structure and an anatomical body part of the associated patient and describing a relative position between the reference structure and a predetermined reference position;
acquiring thermal image data describing a digital thermal image of the reference structure;
acquiring imaging device position data describing a relative position between the reference structure and an associated thermal imaging device used for taking the digital thermal image and describing a predetermined relative position between the associated thermal imaging device and the predetermined reference position;
determining, based on the planning image data, planning image pattern data describing a planning image pattern in the digital planning image assigned to a representation of the reference structure;
determining, based on the thermal image data, thermal image pattern data describing a thermal image pattern in the digital thermal image assigned to the representation of the reference structure;
determining positional difference data based on: the reference structure position data, the imaging device position data, the planning image pattern data, and the thermal image pattern data, the positional difference data describing a difference between:
a relative position between the anatomical body part of the associated patient and the predetermined reference position at a point in time at which the planning image data was generated, and
a relative position between the anatomical body part of the associated patient and the predetermined reference position at a point in time at which the thermal image data was generated.

16. The non-transitory computer-readable program storage medium according to claim 15, wherein the program stored thereon is executable by the computer of the associated patient pre-positioning apparatus for further supporting the pre-positioning by:
acquiring planning image data describing a digital planning image of:
a face of the associated patient; and
an open face mask medical device attached to the face of the associated patient, the open face mask medical device defining a contour in the planning image data, wherein the planning image pattern data describes the contour as the planning image pattern.

17. A system for supporting positioning a patient for at least one of radiotherapy treatment or radiosurgery, the system comprising:
a) a computer operable to:
acquire planning image data describing a digital planning image of a reference structure;
acquire reference structure position data describing a predetermined relative position between the reference structure and an anatomical body part of the associated patient and describing a relative position between the reference structure and a predetermined reference position;
acquire thermal image data describing a digital thermal image of the reference structure;
acquire imaging device position data describing a relative position between the reference structure and an associated thermal imaging device used for taking the digital thermal image and describing a predetermined relative position between the associated thermal imaging device and the predetermined reference position;
determine, based on the planning image data, planning image pattern data describing a planning image pattern in the digital planning image assigned to a representation of the reference structure;

determine, based on the thermal image data, thermal image pattern data describing a thermal image pattern in the digital thermal image assigned to the representation of the reference structure;

determine positional difference data based on: the reference structure position data, the imaging device position data, the planning image pattern data, and the thermal image pattern data, the positional difference data describing a difference between:

a relative position between the anatomical body part of the associated patient and the predetermined reference position at a point in time at which the planning image data was generated, and a relative position between the anatomical body part of the associated patient and the predetermined reference position at a point in time at which the thermal image data was generated;

b) an electronic data storage device storing at least the planning image data, the reference structure position data and the imaging device position data;

c) a thermal imaging device receiving the digital thermal image, the thermal imaging device being operably coupled to the at least one computer for transmitting a signal to the at least one computer corresponding to the thermal image data;

d) a treatment device usable for treating the patient with the at least one of the radiotherapy treatment or the radiosurgery; and e) a patient support unit for supporting the patient's body, wherein the computer is operably coupled with the at least one electronic data storage device for acquiring, from the at least one data storage device, the planning image data, the reference structure position data and the imaging device position data, wherein the computer is operably coupled to at least one of the treatment device or the patient support unit.

* * * * *